United States Patent [19]

Kelly

[11] 4,202,971
[45] May 13, 1980

[54] ENLARGED-HETERO-RING PROSTACYCLIN ANALOGS

[75] Inventor: Robert C. Kelly, Kalamazoo, Mich.

[73] Assignee: The Upjohn Company, Kalamazoo, Mich.

[21] Appl. No.: 12,263

[22] Filed: Feb. 15, 1979

Related U.S. Application Data

[60] Division of Ser. No. 935,291, Aug. 21, 1978, which is a division of Ser. No. 819,941, Jul. 28, 1977, Pat. No. 4,124,599, which is a continuation-in-part of Ser. No. 725,547, Sep. 22, 1976, abandoned, which is a continuation-in-part of Ser. No. 716,771, Aug. 23, 1976, abandoned.

[51] Int. Cl.² .................................................. C07D 311/94
[52] U.S. Cl. .................................. 542/426; 542/429; 260/345.2
[58] Field of Search .................. 260/345.2 P; 542/426, 542/429

[56] References Cited

U.S. PATENT DOCUMENTS 3,435,053   3/1969   Beal ..................................... 260/345.2

*Primary Examiner*—Robert Gerstl
*Attorney, Agent, or Firm*—Robert A. Armitage

[57] ABSTRACT

Prostaglandin ($PG_1$) derivatives having (1) a 6-keto feature, together with a 9-deoxy-9-hydroxymethyl feature for example

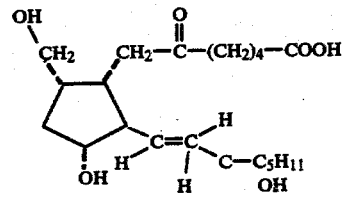

or (2) a 9-deoxy-6,9-epoxymethano feature together with a 5-halo or 6-hydroxy feature, for example

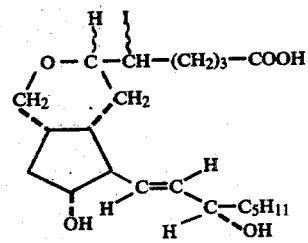

or

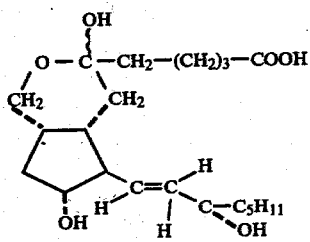

or a 5,6-didehydro feature, for example in an enol ether of the formula

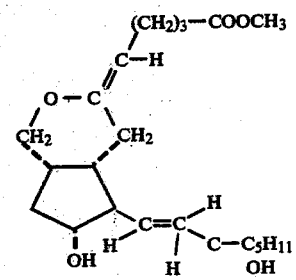

said derivatives having pharmacological activity. Processes for preparing them and the appropriate intermediates are disclosed.

17 Claims, No Drawings

ENLARGED-HETERO-RING PROSTACYCLIN ANALOGS

CROSS REFERENCE TO RELATED APPLICATIONS

This application is a division of copending application Ser. No. 935,291, filed Aug. 21, 1978, which was a division of then copending application Ser. No. 819,941, filed July 28, 1977, now issued as U.S. Pat. No. 4,124,599, which was a continuation-in-part of then copending application Ser. No. 725,547, filed Sept. 22, 1976, since abandoned, which was a continuation-in-part of then copending application Ser. No. 716,771, filed Aug. 23, 1976, since abandoned.

BACKGROUND OF THE INVENTION

This invention relates to prostaglandin derivatives and to a process for preparing them.

The prostaglandins and analogs are well-known organic compounds derived from prostanoic acid which as the following structure and atom numbering:

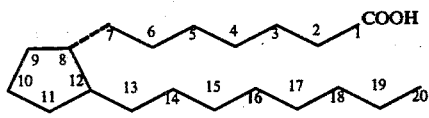

As drawn hereinafter the formulas represent a particular optically active isomer having the same absolute configuration as PGE$_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background on prostaglandins, see for example Bergstrom et al., Pharmacol. Rev. 20, 1 (1968). For related compounds see Pace-Asciak et al., Biochem. 10, 3657 (1971). Related compounds are described in a publication on 6-keto-prostaglandin F$_{1\alpha}$ by Pace-Asciak, J. Am. Chem. Soc. 98, 2348 (1976) and a publication on "PGX" (6,9α-oxido-9α,15α-dihydroxy-prosta-(Z)5,(E)13-dienoic acid) by E. J. Corey et al., J. Am. Chem. Soc. 99, 20006 (1977).

Some of the compounds of this invention may be regarded as analogs of prostacyclin and prostacyclin-type compounds.

Prostacyclin, an organic compound related to prostaglandins, is (5Z)-9-deoxy-6,9α-epoxy-Δ$^5$-PGF$_1$ and is represented by the formula

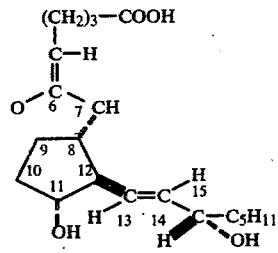

For its synthesis and structure see for example R. A. Johnson et al., J. Am. Chem. Soc. 99, 4182 (1977) and Prostaglandins 12, 915 (1976), and E. J. Corey et al., cited above. For some of its biological properties and uses see the references cited in the Johnson references. Prostacyclin is referred to as "PGI$_2$", see Anonymous, Prostaglandins 13, 375 (1977).

The essential material for this application, including the background of the invention, the disclosure of the invention, and the description of the preferred embodiments, including Preparations and Examples, is incorporated by reference from the commonly owned U.S. Pat. No. 4,124,599 issued on Nov. 7, 1978, under the provisions of M.P.E.P. 608.01(p).

SUMMARY OF THE INVENTION

It is the purpose of this invention to provide novel products having pharmacological activity. It is a further purpose to provide processes for preparing these products and their intermediates.

Accordingly, there is provided a compound of the formula:

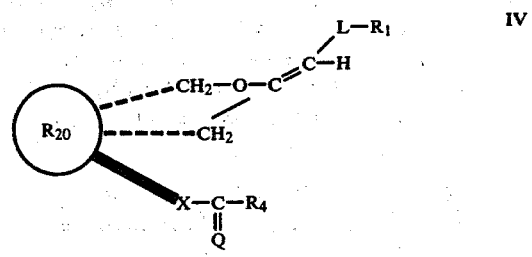

or a mixture comprising that compound and the enantiomer thereof wherein R$_{20}$ is

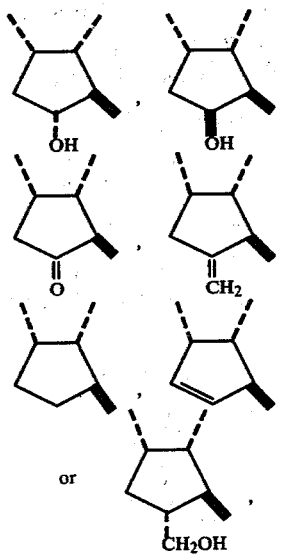

wherein L is (1) —(CH$_2$)$_d$—C(R$_2$)$_2$—

(2) —CH$_2$—O—CH$_2$—Y— or (3) —CH$_2$CH=CH— wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—, wherein Q is

wherein R$_8$ is hydrogen or alkyl of one to 4 carbon atoms, inclusive, wherein R$_1$ is
(1) —COOR$_3$
(2) —CH$_2$OH
(3) —CH$_2$N(R$_9$)(R$_{18}$)

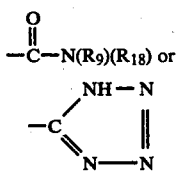

(4)

(5)

wherein R$_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms,

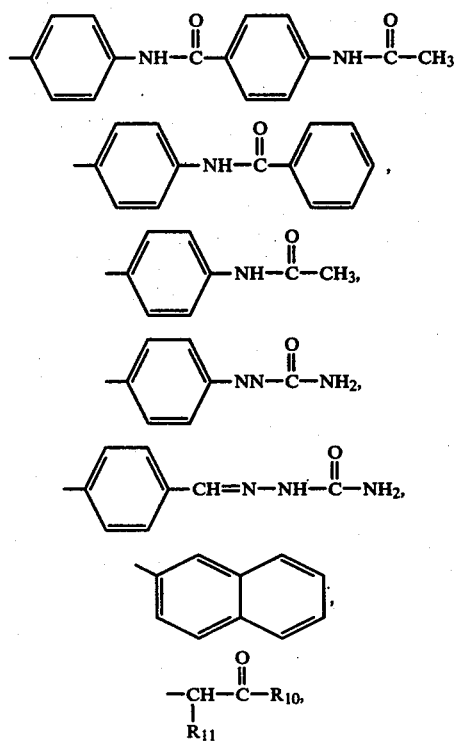

(g)

(h)

(i)

(j)

(k)

(l)

(m)

wherein R$_{10}$ is phenyl, p-bromophenyl, p-biphenylyl, p-nitrophenyl, p-benzamidophenyl, or 2-naphthyl, and wherein R$_{11}$ is hydrogen or benzoyl or (n) a pharmacologically acceptable cation, wherein R$_9$ is hydrogen, methyl, or ethyl, and R$_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein R$_4$ is

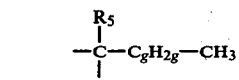

(1)

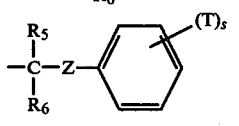

(2)

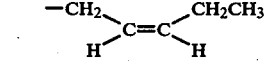

(3)

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro when the other is hydrogen or fluoro and the further proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive, between CR$_5$R$_6$- and the phenyl ring; wherein T is alkyl of one to 4 carbon atoms, inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans—CH=CH—
(2) cis—CH=CH—
(3) —C≡C— or
(4) —CH$_2$CH$_2$—;

including the lower alkanoates thereof.

In formula IV as used herein, attachment to R$_{20}$ corresponds to bonds to the cyclopentane ring at the C—8, C—9, and C—12 positions following prostaglandin nomenclature, thus:

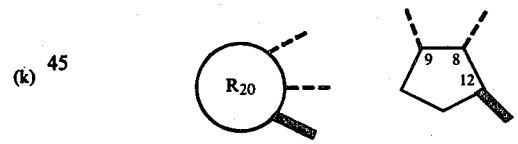

Within the scope of the prostaglandin derivatives described herein there are represented (a) PGF$_\alpha$ compounds when R$_{20}$ is

(b) 11β-PGF$_\alpha$ compounds when R$_{20}$ is

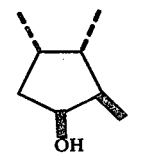

(c) 11-Deoxy-11-keto-PGFα compounds when ⓇR20 is

;

(d) 11-Deoxy-11-methylene-PGFα compounds when ⓇR20 is

;

(e) 11-Deoxy-PGFα compounds when ⓇR20 is

;

(f) 11-Deoxy-10,11-Didehydro-PGFα compounds when ⓇR20 is

; and (g) 11-Deoxy-11-hydroxymethyl-PGFα compounds when ⓇR20 is

For those compounds of formula IV wherein Q is i.e. wherein the C-15 hydroxyl group is attached to the side chain in alpha configuration, the configuration at C-15 is identical with that of the naturally occuring prostaglandins such as PGE$_1$ obtained from mammalian tissues. The 15-epimer compounds are represented by formula IV when Q is and are identified variously as "15-epi" or "15β" or "15R" by the appropriate prefix in the name. As is known in the art, "R" and "S" designations depend on the neighboring substituents. See R. S. Cahn, J. Chem. Ed. 41, 116 (1964).

Also included within the scope of this invention are compounds of the formula

XXI wherein L, Q, R$_1$, R$_4$, ⓇR20, and X are as defined herein.

I claim:
1. A 5Z compound of the formula wherein ⓇR20 is or wherein L is
(1) —(CH$_2$)$_d$—C(R$_2$)$_2$—
(2) —CH$_2$—O—CH$_2$—Y— or
(3) —CH$_2$CH=CH—
wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein Q is wherein R$_8$ is hydrogen or alkyl of one to 4 carbon atoms, inclusive, wherein R₃ is (a) cycloalkyl of 3 to 10 carbon atoms, inclusive, (b) aralkyl of 7 to 12 carbon atoms, inclusive, (c) phenyl, (d) phenyl substituted with one, 2, or 3 chloro or alkyl of one to 4 carbon atoms, inclusive, (e) 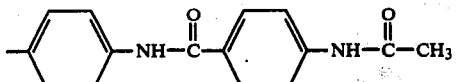

(f) 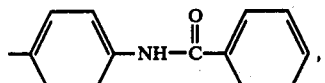

(g) 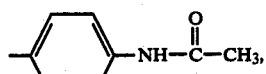

(h) 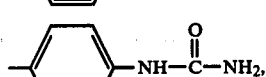

(i) 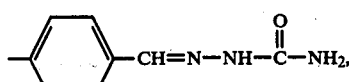

(j) 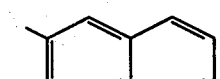, or (k) 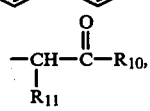

wherein R₁₀ is phenyl, p-bromophenyl, p-biphenylyl, p-nitrophenyl, p-benzamidophenyl, or 2-naphthyl, and wherein R₁₁ is hydrogen or benzoyl; wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or C$_j$H$_{2j}$ wherein C$_j$C$_{2j}$ is a valence bond or alkylene of one to 9 carbon atoms, inclusive, with one to 6 carbon atoms, inclusive between CR₅R₆— and the phenyl ring;

wherein T is alkyl of one to 4 carbon atoms, inclusive, fluoro, chloro, trifluoromethyl, or —OR₇— wherein R₇ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans—CH=CH—
(2) cis—CH=CH—
(3) —C≡C— or
(4) —CH₂CH₂—;

including the lower alkanoates thereof.

2. A compound according to claim 1 wherein R₂₀ is

3. A compound according to claim 1 wherein R₂₀ is

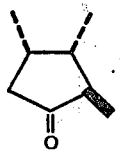

4. A compound according to claim 1 wherein R₂₀ is

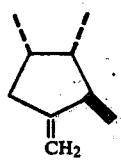

5. A compound according to claim 1 wherein R₂₀ is

6. A compound according to claim 1 wherein R₂₀ is

7. A compound according to claim 1 wherein R₂₀ is

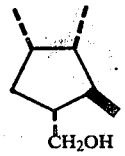

8. A compound according to claim 1 wherein R₂₀ is

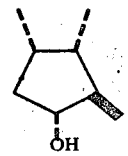

9. A compound according to claim 8 wherein L is —(CH₂)$_n$—, n being 3, 4, or 5, wherein Q is

wherein R₈ is hydrogen, methyl, or ethyl, and wherein

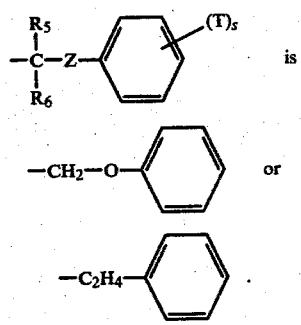 is

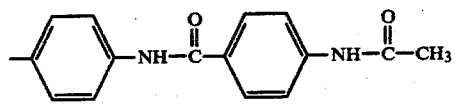 or

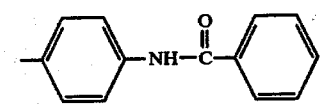

10. A compound according to claim 9 wherein X is —C≡C—.

11. A compound according to claim 9 wherein X is —CH₂CH₂—.

12. A compound according to claim 9 wherein X is trans—CH=CH—.

13. A compound according to claim 12 wherein R₃ is

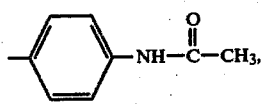

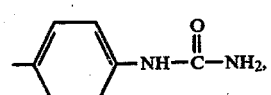

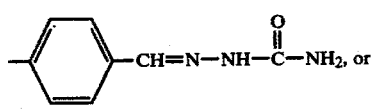

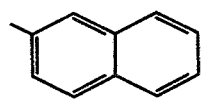,

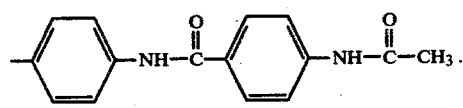

14. (5Z)-9-Deoxy-6,9α-epoxymethano-Δ⁵-17-phenyl-18,19,20-tri-nor-PGF₁, p-(p-acetamidobenzamido)phenyl ester, a compound according to claim 13 wherein R₃ is

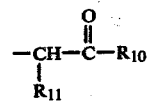

15. A compound according to claim 12 wherein R₃ is

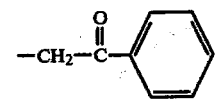

wherein R₁₀ is phenyl, p-bromophenyl, p-biphenylyl, p-nitrophenyl, p-benzamidophenyl, or 2-naphthyl, and wherein R₁₁ is hydrogen or benzoyl.

16. (5Z)-9-Deoxy-6,9α-epoxymethano-Δ⁵-phenoxy-17,18,19,20-tetranor-PGF₁, phenacyl ester, a compound according to claim 15 wherein R₃ is

17. A 5E compound of the formula

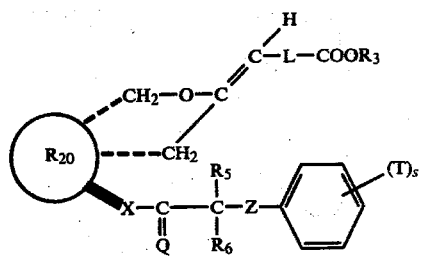

wherein R₂₀ is

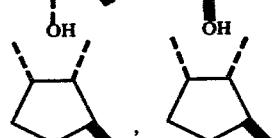,

,

,

,

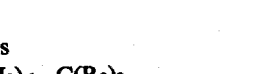,

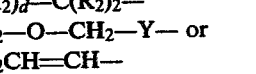 or

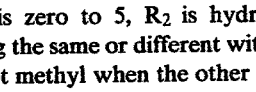, wherein L is
(1) —(CH₂)_d—C(R₂)₂—
(2) —CH₂—O—CH₂—Y— or
(3) —CH₂CH=CH—
wherein d is zero to 5, R₂ is hydrogen, methyl, or fluoro, being the same or different with the proviso that one R₂ is not methyl when the other is fluoro, and Y is a valence bond, —CH₂— or (CH₂)₂—, wherein Q is

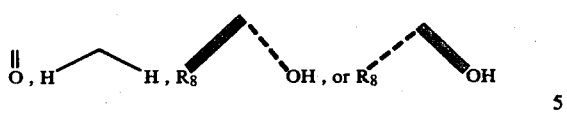

wherein $R_8$ is hydrogen or alkyl of one to 4 carbon atoms, inclusive,
wherein $R_3$ is (a) cycloalkyl of 3 to 10 carbon atoms, inclusive, (b) aralkyl of 7 to 12 carbon atoms, inclusive, (c) phenyl, (d) phenyl substituted with one, 2, or 3 chloro or alkyl of one to 4 carbon atoms, inclusive,

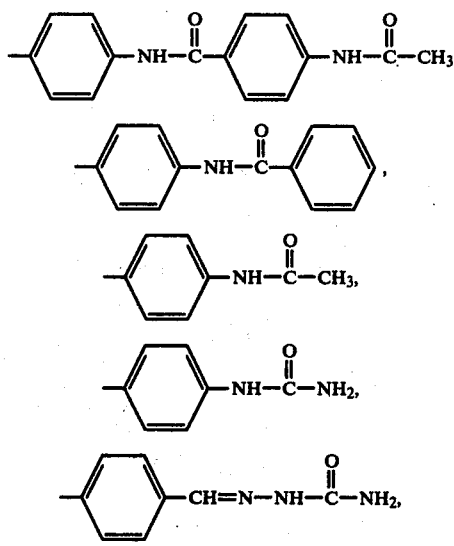

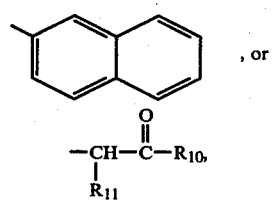

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl; wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jC_{2j}$ is a valence bond or alkylene of one to 9 carbon atoms, inclusive, with one to 6 carbon atoms, inclusive between $CR_5R_6$— and the phenyl ring;
wherein T is alkyl of one 4 carbon atoms, inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different; and
wherein X is
  (1) trans—CH=CH—
  (2) cis—CH=CH—
  (3) —C≡C— or
  (4) —CH$_2$CH$_2$—;
including the lower alkanoates thereof.

UNITED STATES PATENT OFFICE
CERTIFICATE OF CORRECTION

Patent No. 4,202,971           Dated 13 May 1980

Inventor(s) Robert C. Kelly

It is certified that error appears in the above-identified patent and that said Letters Patent are hereby corrected as shown below:

Column 1, lines 55-63, that portion of the formula reading

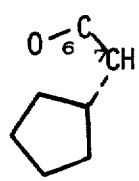   should read   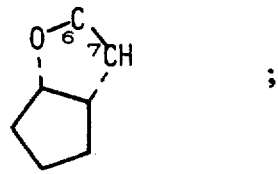  ;

Column 3, lines 42-44,

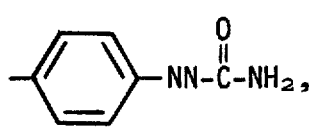   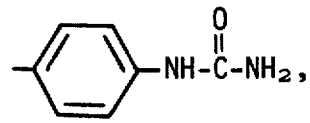

Column 9, line 68, through Column 10, line 10, cancel claim 15;

Column 10, lines 11-12, "$\Delta^5$---phenoxy-" should read -- $\Delta^5$-16-phenoxy- --;

Column 10, line 13, "according to claim 15" should read -- according to claim 12 --;

UNITED STATES PATENT OFFICE
CERTIFICATE OF CORRECTION

Patent No. 4,202,971    Dated 13 May 1980

Inventor(s) Robert C. Kelly

It is certified that error appears in the above-identified patent and that said Letters Patent are hereby corrected as shown below:

Column 12, line 35, new claim 18, as follows:

--- A compound according to claim 12, wherein $R_3$ is

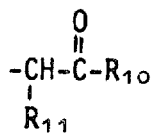

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl. --   .

Signed and Sealed this

*Seventh* Day of *April 1981*

[SEAL]

*Attest:*

RENE D. TEGTMEYER

*Attesting Officer*    *Acting Commissioner of Patents and Trademarks*